US012788449B2

(12) United States Patent
Forbes et al.

(10) Patent No.: US 12,788,449 B2
(45) Date of Patent: Nov. 10, 2026

(54) PLATE FOR SURGICAL FUSION DESIGNED FOR TRANSNASAL PLACEMENT

(71) Applicant: University of Cincinnati, Cincinnati, OH (US)

(72) Inventors: Jonathan Forbes, Cincinnati, OH (US); Justin Virojanapa, Cincinnati, OH (US); Joseph Cheng, Cincinnati, OH (US); Ahmed Hussein, Cincinnati, OH (US); Norberto Andaluz, Cincinnati, OH (US); Sanjit Shah, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 18/533,092

(22) Filed: Dec. 7, 2023

(65) Prior Publication Data

US 2024/0188995 A1 Jun. 13, 2024

Related U.S. Application Data

(60) Provisional application No. 63/430,745, filed on Dec. 7, 2022.

(51) Int. Cl.
*A61B 17/70* (2006.01)
*A61B 17/68* (2006.01)

(52) U.S. Cl.
CPC ........ *A61B 17/7055* (2013.01); *A61B 17/683* (2013.01); *A61B 2017/681* (2013.01)

(58) Field of Classification Search
CPC .................................................. A61B 17/7058
See application file for complete search history.

(56) References Cited

U.S. PATENT DOCUMENTS

2004/0102773 A1* 5/2004 Morrison ............. A61B 17/701 606/70
2014/0188178 A1* 7/2014 Juchno ............... A61B 17/8047 606/292
2019/0099205 A1* 4/2019 Pisharodi .............. A61F 2/4455
2020/0121370 A1* 4/2020 Finn ................... A61B 17/7043

* cited by examiner

*Primary Examiner* — Tessa M Matthews
(74) *Attorney, Agent, or Firm* — Brent M. Peebles

(57) ABSTRACT

An implant system for the fusion of the occipitocervical (O-C1) joint is provided. The system has a plate including a horizontal panel, a right vertical panel and a left vertical panel. The horizontal panel has at least two openings. The right vertical panel has at least two openings. The left vertical panel has at least two openings. The system also includes at least four bone fixation fasteners to fix the panels to the occipital condyle and C1 lateral mass using the openings in the panels.

4 Claims, 20 Drawing Sheets

PLATE FOR SURGICAL FUSION DESIGNED FOR TRANSNASAL PLACEMENT

CROSS REFERENCE TO RELATED APPLICATIONS

This application claims priority to U.S. Provisional Application Ser. No. 63/430,745, filed Dec. 7, 2022, which application is hereby incorporated by reference in its entirety.

TECHNICAL FIELD

The present invention relates to a method and device for treating occipitocervical arthrodesis. More specifically, this invention relates to an endoscopic endonasal surgical approach for implanting an O-C1 plate.

BACKGROUND OF THE INVENTION

Following odontoidectomy, it is common for patients to develop instability of craniocervical junction (CCJ) and require subsequent instrumented arthrodesis. While this has historically been performed in a staged manner utilizing posterior instrumentation, a small number of case series/reports have described odontoidectomy and C1-2 arthrodesis through a single-stage endonasal approach. There is a paucity of information in the literature regarding optimal methods to expose the ventral CCJ in a safe manner mindful of locoregional anatomy in considering the possibility of endonasal instrumentation.

SUMMARY OF THE INVENTION

The present invention is a novel endonasal method for implanting an O-C1 plate for surgical fusion. One embodiment of the present invention an implant system for the fusion of the occipitocervical (O-C1) joint. The system has a plate comprising a horizontal panel, a right vertical panel and a left vertical panel. The horizontal panel has at least a first opening and a second opening. The right vertical panel has at least a first right vertical panel opening and a second right vertical panel opening. The left vertical panel has at least a first left vertical panel opening and a second left vertical panel opening. The system also includes at least four bone fixation fasteners. A first fastener is disposed with both the first opening and the first right vertical panel opening. A second fastener is disposed with both the second opening and the first left vertical panel opening. A third fastener is disposed with the second right vertical panel opening. A fourth fastener is disposed with the second left vertical panel opening. In addition, the first fastener is engageable with the plate and capable of fixing with the C1 lateral mass. The second fastener is engageable with the plate and capable of fixing with the C1 lateral mass. The third fastener is engageable with the plate and capable of fixing with the occipital condyle. The fourth fastener is engageable with the plate and capable of fixing with the occipital condyle.

In one embodiment, the plate comprises a material selected from the group consisting of carbon fiber, polylactic acid, stainless steel alloys, commercially pure titanium, titanium alloys, ceramics, thermoplastics, polyethylene terephthalate (PET), fabric, silicone, polyurethane, silicone-polyurethane copolymers, polymeric rubbers, polyolefin rubbers, hydrogels, semi-rigid and rigid materials. In another embodiment, the plate comprises carbon fiber. In one embodiment, the bone fixation fasteners are selected from the group consisting of bone screws, helical nails, distally expanding nails, and distally expanding screws.

In another embodiment of the present invention, an atlanto-occipital fusion method for fixating a 0-C1 joint is provided. The method involves preparing an endonasal surgical path using a binostril approach. The binostril approach involves removing the inferior portion of the posterior septum, performing a myomucosal flap incision to create a flap, retracting the flap to expose the O-C1 joint, bilaterally decorticating the O-C1 joint, and inserting an implant into each side of the decorticated 0-C1 joint. The implant comprises the implant system described above.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

DETAILED DESCRIPTION

Figure 1:
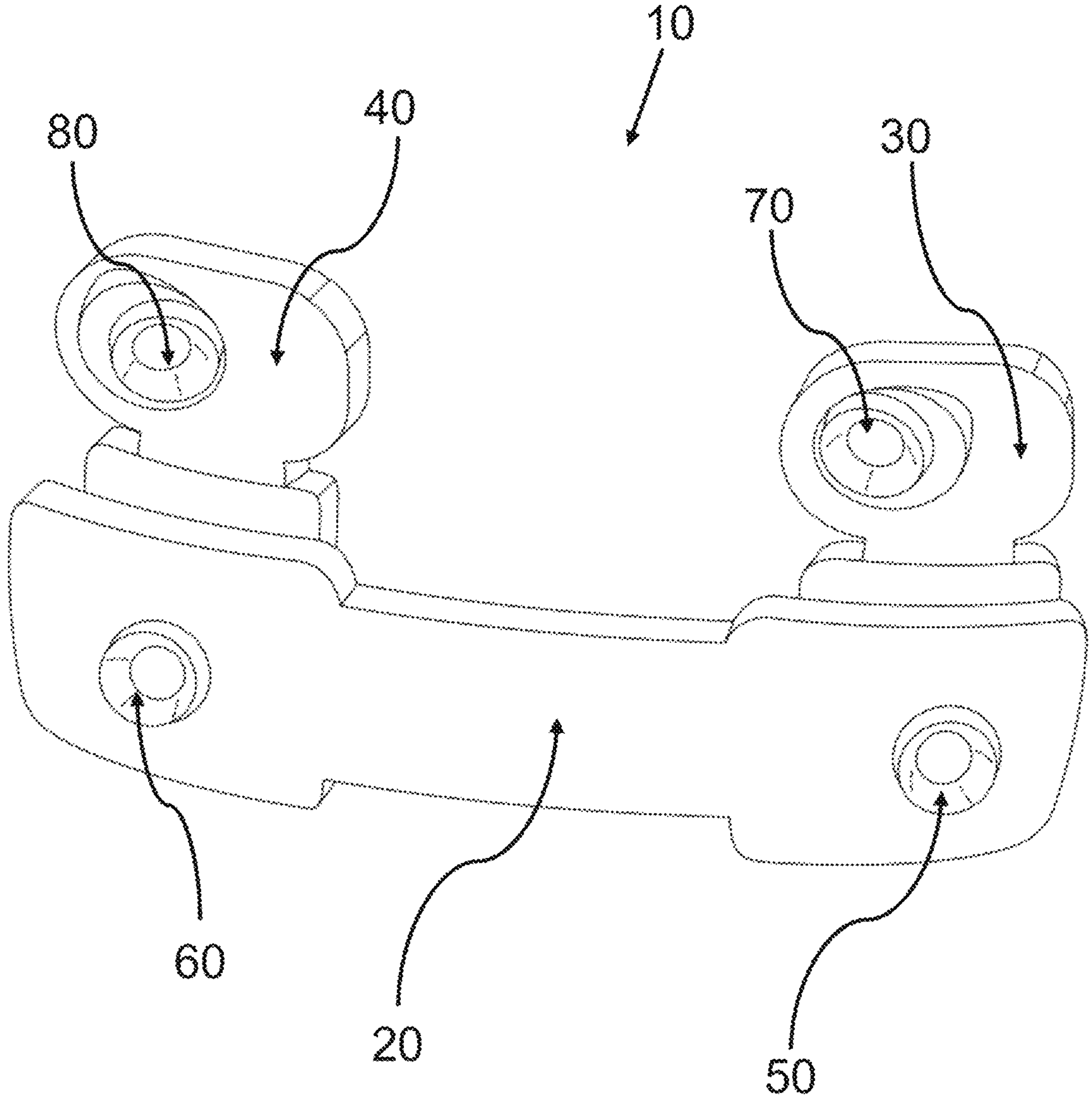
FIG. 1 is a perspective view of an embodiment of the plate of the present invention.

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

While the following terms are believed to be well understood by one of ordinary skill in the art, definitions are set forth to facilitate explanation of the disclosed subject matter. Unless defined otherwise, all technical and scientific terms used herein have the same meaning as commonly understood by one of ordinary skill in the art to which the disclosed subject matter belongs.

Certain terminology is used in the following description for convenience only and is not limiting. The words "right", "left", "lower" and "upper" designate directions in the drawings to which reference is made. The words "inwardly" or "proximally" and "outwardly" or "distally" refer to directions toward and away from, respectively, the geometric center of the implant and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Similar reference numerals will be utilized throughout the application to describe similar or the same components of each of the preferred embodiments of the implant described herein and the descriptions will focus on the specific features of the individual embodiments that distinguish the particular embodiment from the others As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

Occipitocervical (OC) arthrodesis is used to treat instability involving the occipitocervical (O-C1 joint). Currently available O-C fixation devices rely on posterior approaches to the occiput and atlas which involve a considerable amount of muscle dissection, post-operative pain, and blood loss. Our method for arthrodesis utilizes the endonasal corridor to gain access to the basi-occiput and C1 for placement of instrumentation and fusion.

FIGS. 1-6 show an embodiment of the O-C1 plate of the present invention. Referring to FIG. 1, the plate includes two vertical panels 30 and 40. These connect O-C1 bilaterally (the distance between the two screw entry points is initially variable; after stabilization, this distance becomes fixed). Additionally, the plate includes a horizontal panel 20 that connects from C1 (right) to C1 (left) to provide rotational stability.

The plate of the present invention provides a minimally invasive method for stabilization across the O-C1 joint through the endonasal corridor. Approaching O-C1 pathology through a minimally invasive corridor should help minimize pain, length of stay, and post-operative disability. In addition, creation of this device may eliminate the need for a two-stage surgery in some of the patient population (e.g. following an endonasal odontoidectomy).

Figure 2:
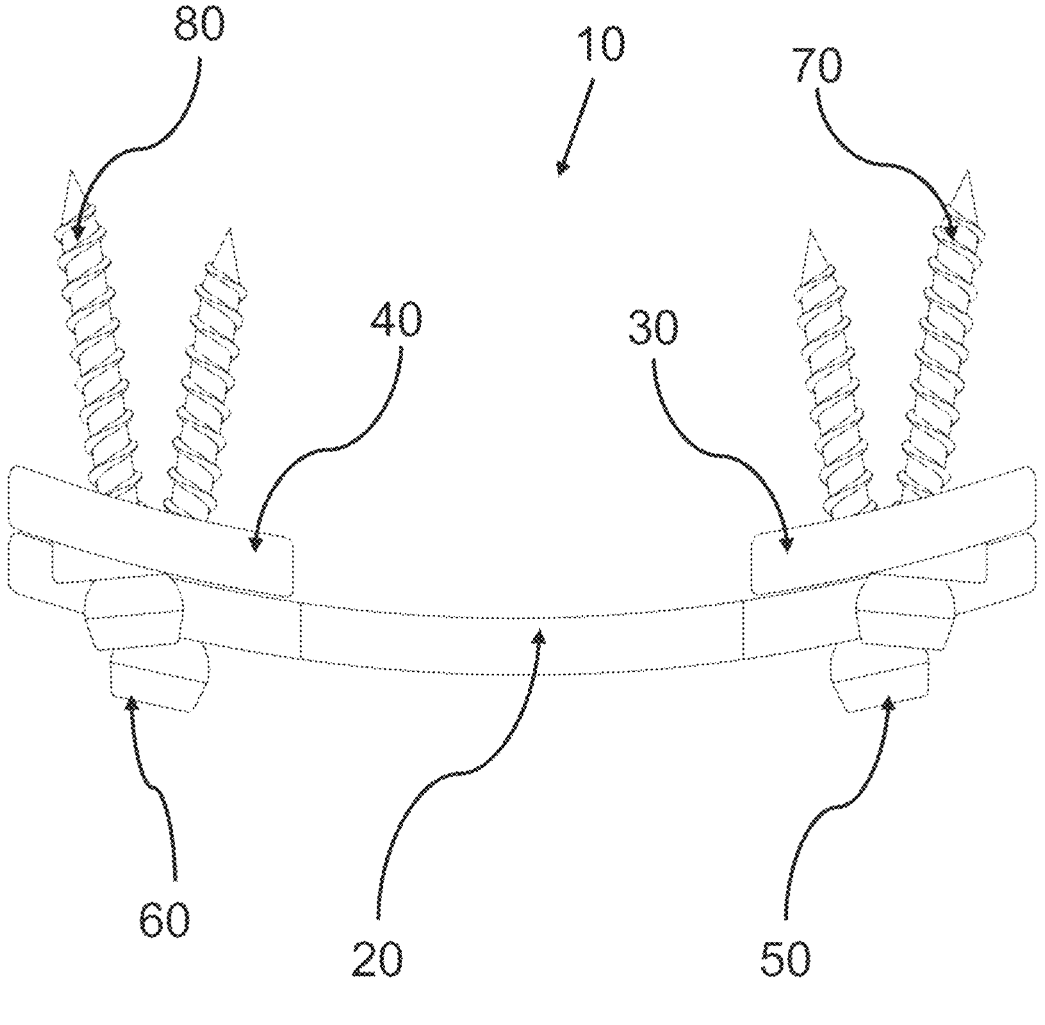
FIG. 2 is a top view of an embodiment of the plate of the present invention including four screws.
Figure 3A:
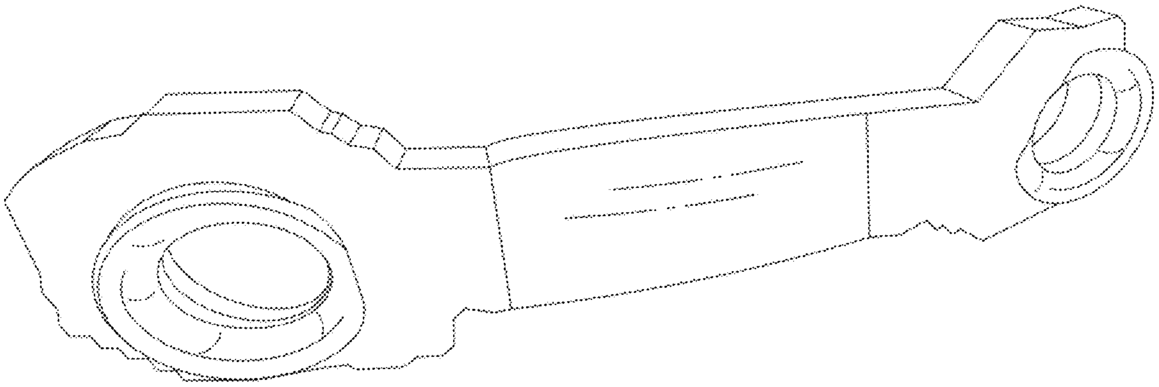
FIG. 3A is a perspective view of an embodiment of the distal horizontal panel portion of the plate of the present invention.
Figure 3B:
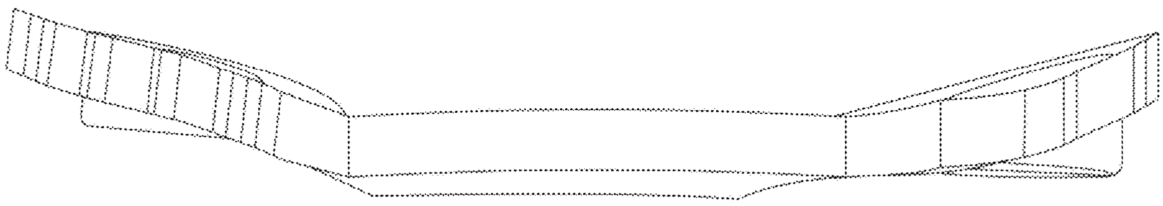
FIG. 3B is a top view of an embodiment of the distal horizontal panel portion of the plate of the present invention.
Figure 3C:
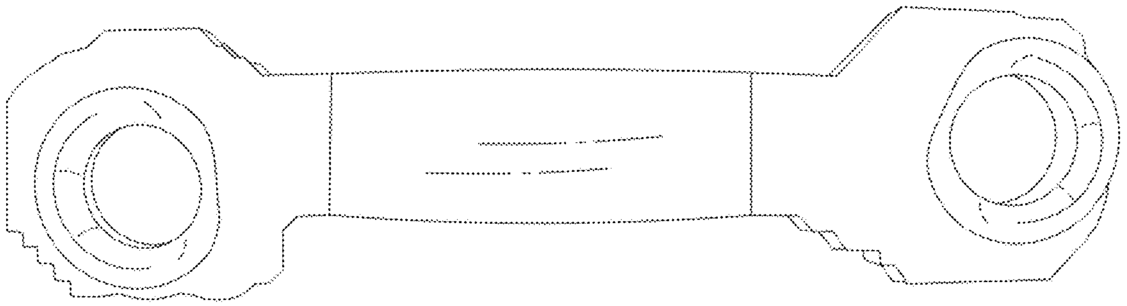
FIG. 3C is a front view of an embodiment of the distal horizontal panel portion of the plate of the present invention.
Figure 3D:
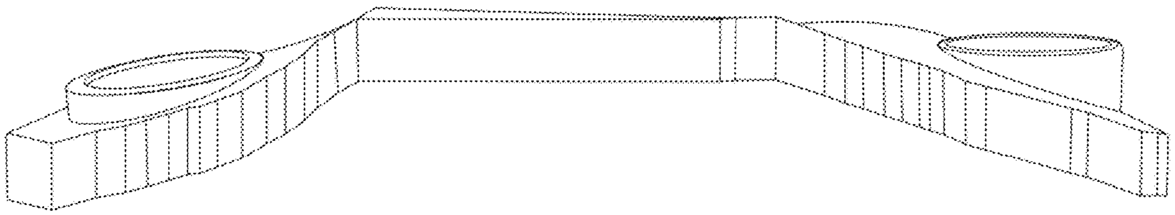
FIG. 3D is a bottom view of an embodiment of the distal horizontal panel portion of the plate of the present invention.
Figure 3E:
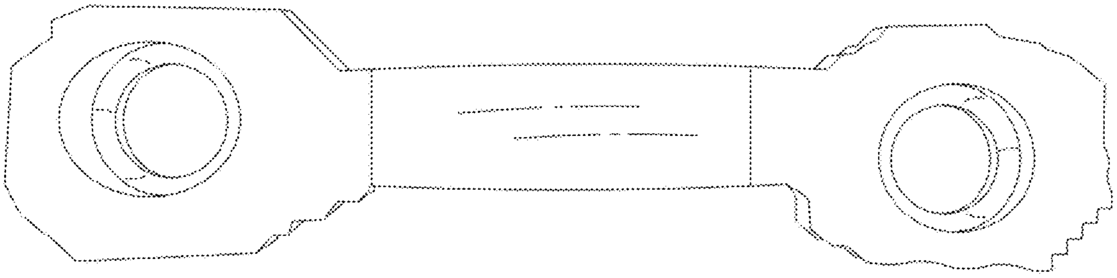
FIG. 3E is a back view of an embodiment of the distal horizontal panel portion of the plate of the present invention.
Figure 4A:
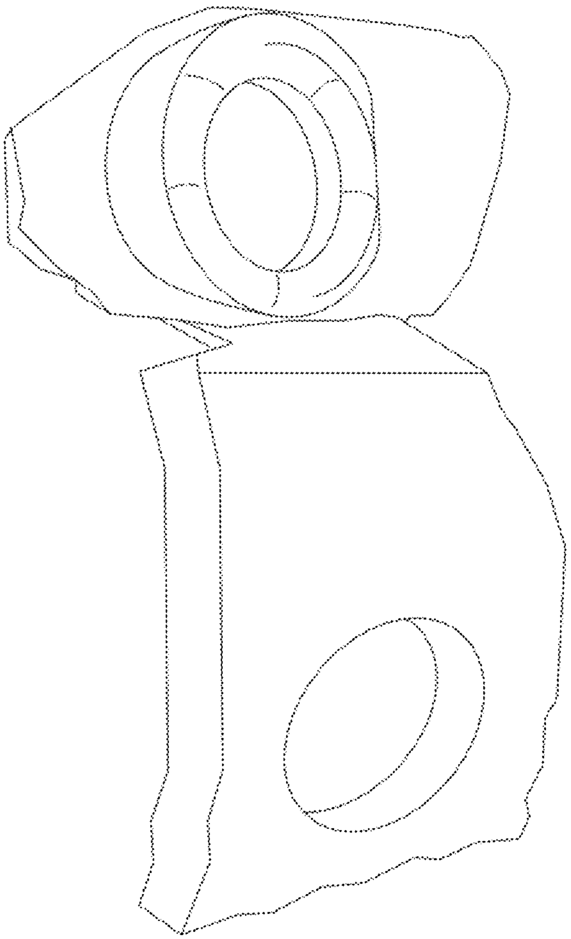
FIG. 4A is a perspective view of an embodiment of the proximal right vertical panel portion of the plate of the present invention.
Figure 4B:
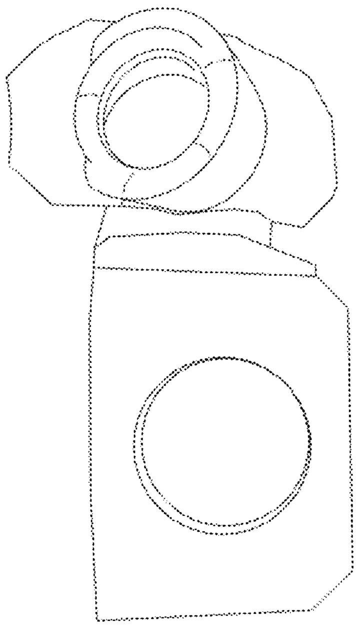
FIG. 4B is a front view of an embodiment of the proximal right vertical panel portion of the plate of the present invention.
Figure 4C:
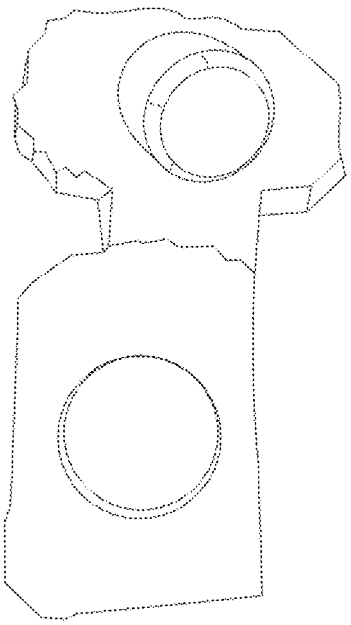
FIG. 4C is a back view of an embodiment of the proximal right vertical panel portion of the plate of the present invention.
Figure 5A:
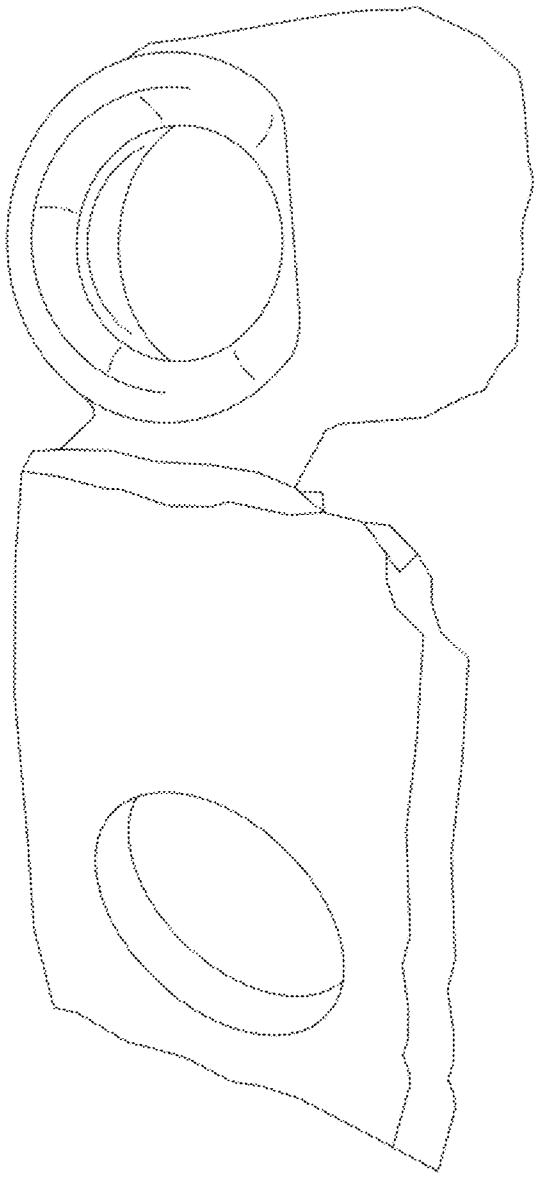
FIG. 5A is a perspective view of an embodiment of the proximal left vertical panel portion of the plate of the present invention.
Figure 5B:
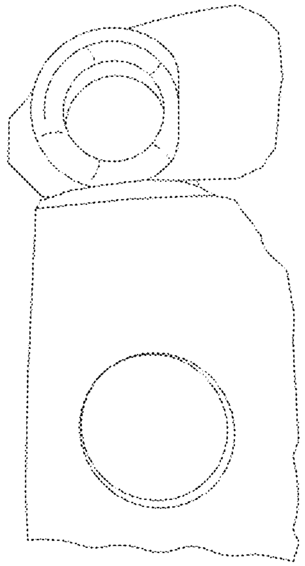
FIG. 5B is a front view of an embodiment of the proximal left vertical panel portion of the plate of the present invention.
Figure 5C:
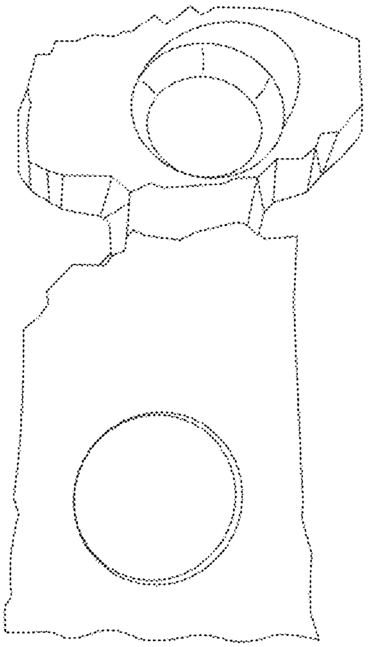
FIG. 5C is a back view of an embodiment of the proximal left vertical panel portion of the plate of the present invention.
Figure 6A:
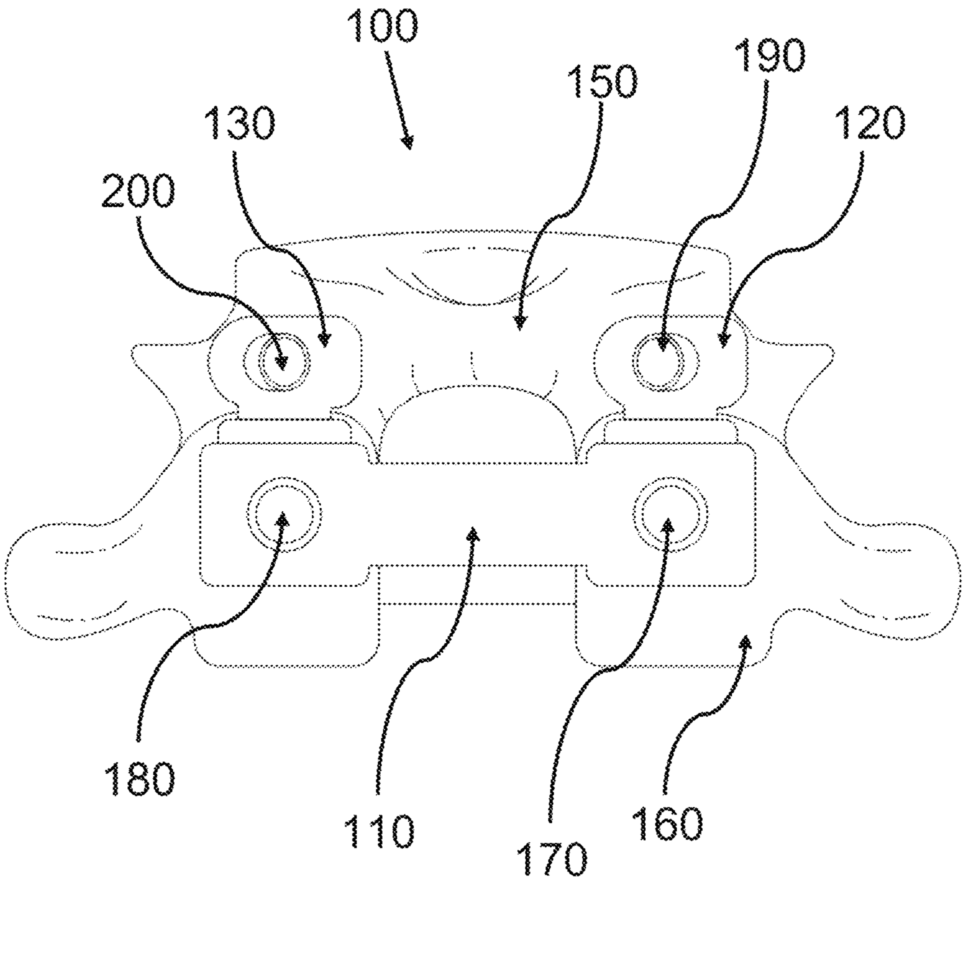
FIG. 6A is a front view of an embodiment of the plate of the present invention.
Figure 6B:
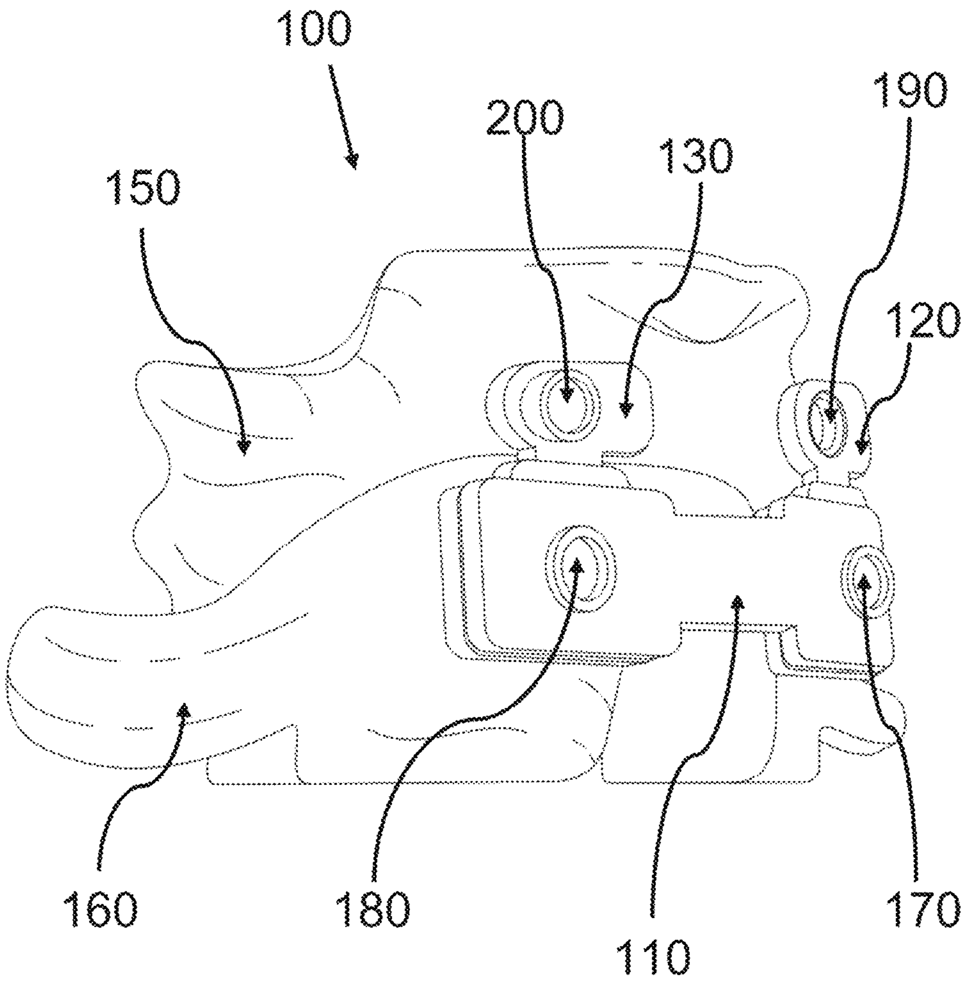
FIG. 6B is a perspective view of an embodiment of the plate of the present invention.

The O-C1 joint is first exposed through the endonasal corridor using methods described herein. The plate is introduced through the nares to the posterior nasopharynx, where it can be directly fixated to both the occipital condyle and the C1 lateral mass. FIGS. 1 and 2 show an implant system 10 according to the present invention. The implant system includes a horizontal panel 20, a right vertical panel 30 and a left vertical panel 40. Bone fixation fasteners 50, 60, 70 and 80 are inserted through openings in the horizontal panel and vertical panels. FIGS. 6A and 6B show the plate 100 fixed on an O-C1 joint (the C1 lateral mass 160 and the occipital condyle 150). The plate has a horizontal panel 110, a right vertical panel 120 and a left vertical panel 130. Bone fixation fasteners 170, 180, 190 and 200 are inserted through openings in the horizontal panel and vertical panels.

In one embodiment, the plate is comprised of titanium. Placement and design of the plate are as follows:

The plate shown in FIGS. 1-6 accommodates variable-angle screws, which are placed using neuro-navigation. The entry site of the anterior condylar screw is approximately 8 mm rostral and 8 mm lateral to the inferomedial O-C joint. The trajectory of the screw is approximately 40 degrees lateral and 15 degrees inferior. The goal is bicortical purchase of the condyle using neuronavigation (approximate screw size is 4 mm×22 mm). The entry site of the C1 screw is at the intersection of the lateral extent of IUBF and the mid-C1 lateral mass. The approximate length of the C1 screw is 4.0×20 mm. The approximate trajectory is 15 degrees lateral.

The plate shown in FIGS. 1-6 is modular. There are two individual panels (right and left). The panels are placed individually. The second panel is than brought to the posterior nasopharynx and used to fixate the contralateral side. At this time, a cross link is used to connect the two panels to enhance biomechanical stability. The site of attachment of the cross link is the region of the panel that houses the locking mechanism.

Endoscopic Endonasal Approach

The primary treatment for reducible, ventral compressive pathology of the craniovertebral junction is reduction and stabilization. In cases in which reduction cannot be achieved, consideration is given to ventral decompression vis-a-vis odontoidectomy. This can be accomplished using transnasal, transoral, or transcervical approaches. The endoscopic endonasal approach (EEA) has been proposed more recently as an alternative corridor especially well-suited to pathology above the palatal line that may be associated with earlier extubation, earlier reinitiation of oral feeds, and lower risk of post-operative velopalatal insufficiency. Patients who undergo odontoidectomy are at risk for post-operative instability involving the atlantoaxial joint and occipitocervical junction. The altered biomechanics at C1-2 and/or O-C1 relate both to damage incurred by the primary pathologic process, as well as additional instability imparted by the odontoidectomy-which often also involves removal of the anterior C1 ring and associated ligamentous structures. In historical series, it was common practice to follow patients longitudinally for development of instability following odontoidectomy prior to scheduling craniocervical fusion. It has become increasingly common in contemporary neurosurgical series for patients to be jointly scheduled for odontoidectomy and staged posterior instrumented fusion during the same hospital stay. These reports suggest an algorithm seeking to define levels necessitating arthrodesis prior to odontoidectomy is a feasible operative strategy to employ.

Previous authors have proposed that a same-stage endonasal method for craniocervical fusion following odontoidectomy would hypothetically eliminate the pain, disability, and risks associated with a separate stage posterior approach. With this strategy in mind, a cadaveric study by Mendes et al. described a novel method of endoscopic endonasal transarticular C1-2 fixation that would permit endonasal decompression and C1-2 fusion in a single-stage procedure. Biomechanical analysis of this endonasal construct was found to be comparable to analogous methods of posterior fixation. Following publication of the Mendes report, clinical descriptions of endonasal C1-2 stabilization following odontoidectomy have reported use of a separate technique with cannulated-screw fixation of the residual C1 ring to the odontoid remnant. These studies add to the separate existing body of knowledge describing previous clinical reports of trans-oral methods for instrumentation that have extended as high as the clivus and as low as C3. Validation of an endonasally-compatible construct able to support O-C1 instrumentation and arthrodesis does not yet exist. Despite the numerous aforementioned investigations, which include multiple clinical descriptions of endonasal and transoral instrumentation, there is a paucity of information in the literature regarding optimal methods to expose the ventral craniocervical junction in a safe and anatomic manner that is mindful of locoregional structures.

The method of the present invention provides at least two advantages: (1) to quantify the ability of an inverted U-shaped buccopharyngeal flap (IUBF) based on regional anatomic landmarks to facilitate endonasal access to the C1-2 and O-C1 joint spaces and (2) to obtain anatomic measurements assessing the distance from required pharyngeal incisions to various, adjacent neurovascular structures.

Reports detailing the placement of spinal instrumentation via a trans-oral corridor to correct instability associated with odontoidectomy have existed for over 20 years. Interestingly, review of the literature has found no evidence to suggest that placement of spinal instrumentation via trans-mucosal or clean-contaminated corridor is associated with increased risk of SSI. In recent years, the endoscopic endonasal approach (EEA) for odontoidectomy has gained favor over the traditional trans-oral corridor; the endonasal approach appears to be especially well-suited to pathology above the palatal line and may be associated with earlier extubation, earlier reinitiation of oral feeds, and lower risk of post-operative velopalatal insufficiency. With increased utilization of the endonasal corridor, it should perhaps come as no surprise that both cadaveric and clinical descriptions now exist in the literature describing trans-nasal placement of spinal instrumentation following endonasal odontoidectomy. However, to the authors' knowledge, no such construct to facilitate occipitocervical arthodesis via an endonasal corridor has been investigated or reported. Despite an increasing number of clinical reports, there is a paucity of information in the literature describing endoscopic techniques for proper exposure of the ventral craniocervical junction-including exposure of O-C1 and C1-2 articulations. While this manuscript does not seek to evaluate the clinical utility of trans-nasal placement of spinal instrumentation, it does endeavor to provide a "roadmap" for optimal exposure of the ventral craniocervical junction in a safe manner mindful of locoregional anatomy.

Kassam et al. provided the first clinical description of an endonasal odontoidectomy in 2005. In this publication, the authors utilized suction electrocautery to outline a U-shaped flap prior to use of a microdebrider for removal of superficial pharyngeal tissue. The longus capitus musculature was then elevated and resected, with care taken to avoid injury to the parapharyngeal carotid arteries. The authors advocated resection of pharyngeal and muscular tissue because of interference with line of sight given lack of a suitable retractor system. Subsequent reports, including the study by Liu et al., have described use of a longitudinal linear midline incision with monopolar electrocautery and subperiosteal elevation of the longus capitis and colli musculature. While such an exposure is sufficient for endonasal odontoidectomy, visualization of O-C1 and/or C1-2 joints was not necessitated or described. In 2015, Mendes et al., demonstrated the feasibility of an endonasal method for C1-2 arthrodesis following odontoidectomy in a cadaveric model. In this study, exposure of the ventral craniocervical junction was obtained following downward reflection of a flap that included nasopharyngeal mucosa and longus capitis and colli musculature. Of note, the rostral incision of this flap was made at the level of the floor of the sphenoid sinus—higher than the level of the pharyngeal tubercle, advocated in this manuscript. While the Mendes study discussed location of the parapharyngeal carotid arteries, the primary intent of the study did not relate to morphometry and the position of the hypoglossal nerves were not defined.

The index study provides information on flap dimensions when incisions are guided by anatomic landmarks that include Rosenmuller's fossae laterally and the pharyngeal tubercle of the clivus superiorly. On average the width of this flap was 26.0 mm at the pharyngeal tubercle and 29.1 mm at the bottom of the flap. The slightly increased width of the bottom of the flap may relate to a more angled trajectory required to perform mucosal incisions posterior to the tubal elevations. Reliance on visual landmarks is an important component of the operative strategy advocated herein. It is important to note that these visual landmarks can be obscured or distorted in cases of younger patients with hypertrophic adenoid tissue, older patients with hypotrophic longus capitus/colli musculature, or patients with medially deviated parapharyngeal ICAs. Our research found the average distance between the carotid arteries was 39.8 mm at C1 and 39.5 mm at the supracondylar groove. In all specimens evaluated, the lateral limbs of the flap did not intersect with the parapharyngeal carotid arteries; however, in 3 of the 10 specimens evaluated, at least one of the two parapharyngeal carotid arteries was noted to reside <5 mm lateral to the lateral limb of the incision. This mean distance between the parapharyngeal carotid arteries reported in this study is in relative agreement with the radiological analysis by Hong et al.—which reported a mean distance from midline of approximately 22 mm. Importantly, the Hong study noted the parapharyngeal internal carotid arteries to be anterior to the medial half of the C1 lateral mass in a small but significant (3.6%) proportion of the patients evaluated; moreover, the ICAs were completely medial to the C1 lateral mass in 0.3% of the patient population. Other studies have reported a significant variability in medial ectasia of the parapharyngeal carotid arteries in the general population, citing the parapharyngeal carotid artery as medial to the lateral mass of C1 in approximately 1% of the population. Based on the aforementioned analyses, the parapharyngeal arteries may be anticipated to be at increased risk of injury with the proposed IUBF in roughly 4% of the patient population. For this reason, routine pre-operative CT angiography prior to employment of the IUBF is recommended. In addition, meticulous inspection of the posterior pharyngeal wall to rule out a pulsatile mass prior to incision should be routinely employed.

Figure 10A:
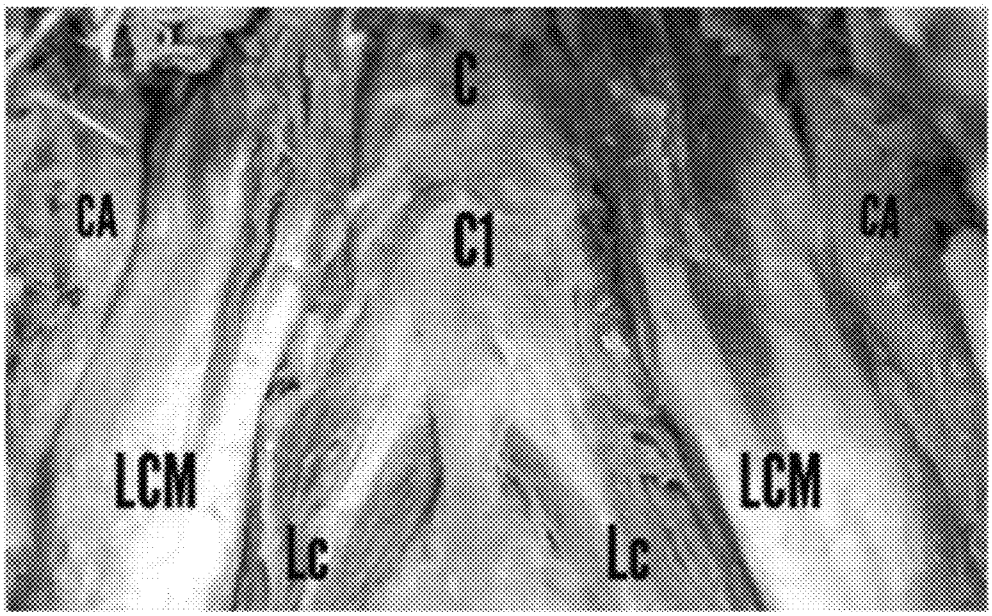
FIG. 10A is an image of the relationships of the longus capitus musculature (LCM) to the carotid artery (CA), anterior C1 ring, longus colli (Lc) musculature and the clivus (C).
Figure 10B:
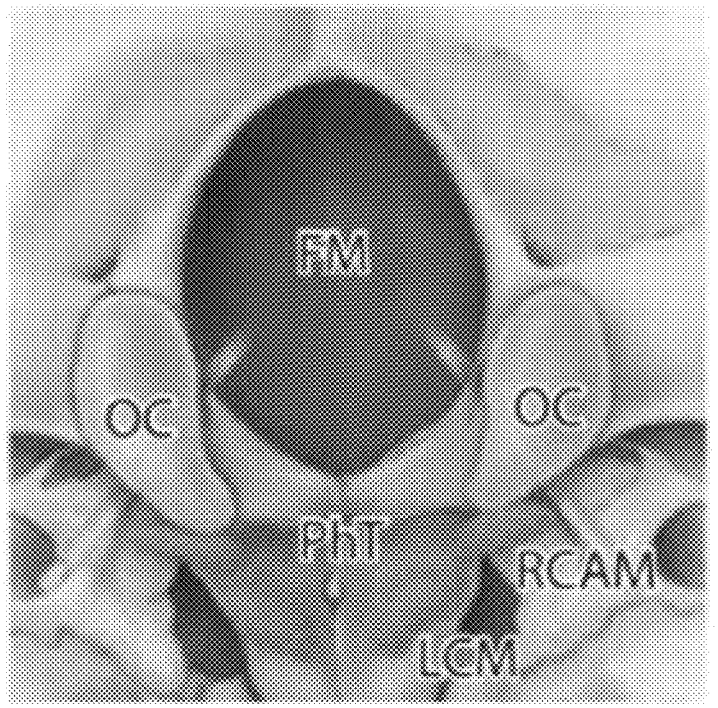
FIG. 10B is an image showing an axial view at level of foramen magnum (FM).
Figure 10C:
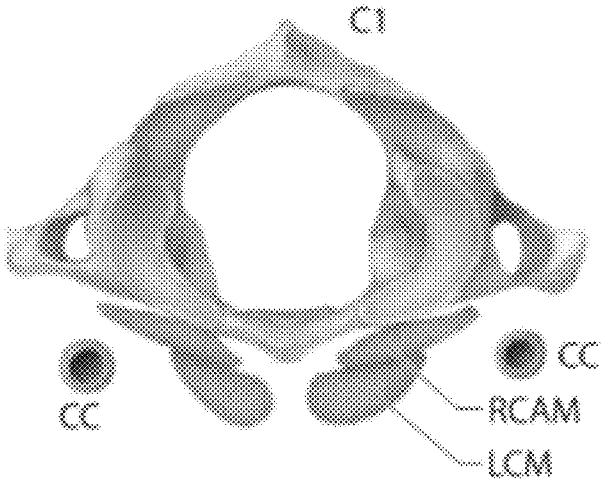
FIG. 10C is an image showing an axial view at level of C1.

In addition to familiarity with location and course of the parapharyngeal internal carotid artery, endoscopic endonasal exposure of the ventral craniocervical junction should proceed with full anatomical knowledge of relevant prevertebral musculature and hypoglossal canal (HC). Following exit from the extracranial hypoglossal foramen, the hypoglossal nerve traverses deep to the planes of the longus capitus (LCM) and rectus capitus anterior (RCAM) muscles. FIGS. 10A-10C depict these relationships in greater detail, which are essential to a proper understanding of ventral access to O-C1 and C1-2 articulations. The LCM is medial and anterior to the plane of the RCAM. This muscle originates from the anterior tubercles of transverse process of C3-6 and ascends upward to insert on the clivus in between the superior and inferior clival lines. The plane of the RCAM is deep to the LCM. This muscle originates from the anterior surface of the lateral mass and transverse process of C1 prior to traveling obliquely upward to insert near the supracondylar groove of the clivus.

FIG. 10A shows the relationships of the longus capitus musculature (LCM) to the carotid artery (CA), anterior C1 ring, longus colli (Lc) musculature and the clivus (C) are depicted. FIG. 10B: (Left) Axial view at level of foramen magnum (FM). The relationships the LCAM and rectus capitus anterior musculature (RCAM) to the O-C1 joints and hypoglossal nerves are depicted. FIG. 10C: Axial view at level of C1. The RCAM and LCM cover the C1-2 articulation. The normal parapharyngeal carotid artery is visible. Abbreviations: OC: occipital condyle, PhT: pharyngeal tubercle.

Figure 11:
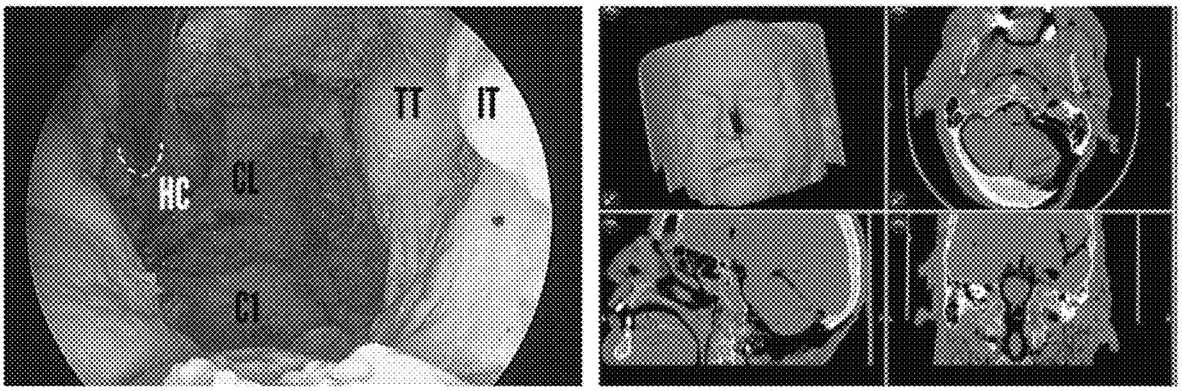
FIG. 11 is a series of images showing the location of the endocranial origin of the hypoglossal canal.

The anatomy of the hypoglossal canal, as encountered via the endoscopic endonasal corridor, has been previously reported by Sreenath et al. and Morera et al. In a study which meticulously described endoscopic endonasal approaches for trans condylar and transjugular corridors, Morera et al. reported the mean distance between extracranial HCs to be 33.9 mm. In this report, the supracondylar groove was recognized as a reliable landmark for localization of the HC. Both the Sreenath and Morera studies advocated resection or lateral reflection of prevertebral musculature for exposure of the HC without further specification. In the index study, the mean distance between HCs of 33.7 mm is in close agreement with the value reported by Morrera et al. FIG. 11 depicts the location of the endocranial origin of the hypoglossal canal, which is visualized in reference to the margins of the IUBF. Importantly, in all 10 specimens evaluated in this study, the lateral limbs of the IUBF did not intersect with the exocranial hypoglossal foramina. However, in seven of ten cadaver heads, the lateral limb of the incision at the level of the supracondylar groove was noted to be <5 mm medial to the HC. In these specimens, the HC was an average of 3.9 mm lateral to the lateral limb of the IUBF. For this reason, neuronavigation may be useful to minimize morbidity associated with hypoglossal nerve injury during procedures in which wide exposure of the ventral craniocervical junction via an endonasal corridor is anticipated. Alternatively, modifications of the rostral margin of the IUBF to maximize exposure of the CCJ and minimize possibility of injury to the hypoglossal nerve may be considered in the future.

FIG. 11: In this cadaveric specimen, cortical bone surrounding the right hypoglossal canal (HC) has been drilled. The location of the endocranial origin of the hypoglossal canal, which is depicted by the tip of the neuronavigation probe, can be visualized in reference to the margins of the IUBF. Abbreviations: CL: clivus, C1: C1 vertebra, TT: torus tubarius, IT: inferior turbinate.

In 2 of the 10 specimens (20%) evaluated in this study, the C1-2 articular surfaces could not be visualized despite aggressive inferior retraction of the soft palate and IUBF. This figure is less than in the study by Mendes et al., in which the authors reported adequate surgical exposure of the C1 and C2 lateral masses in 10 of 10 specimens assessed. In a letter to the editor, the experienced team of Gardner et al. reported difficulty routinely accessing the C1-2 articulation through the endonasal corridor, except in the setting of basilar invagination. It is possible that comparatively more normal craniocervical anatomy in cadaveric specimens (e.g., disproportionately lower incidence of C1-2 anterolisthesis) or uncharacteristically more aggressive methods of retraction used in the cadaveric laboratory may have biased results of this study. Of note, in a manuscript referencing the utility of the nasopalatine line, Kassam et al. reported an average inferior extent of exposure 2.1 cm above the inferior aspect of C2 via the endonasal corridor. This distance, which roughly corresponds to an inferior reach near the C1-2 articulation, is consistent with the authors' clinical experience.

The present invention is the first of its kind to quantify the extent of exposure of the occipitocervical and atlantoaxial articulations via an endoscopic endonasal approach. An IUBF based on regional landmarks of the pharyngeal tubercle and Rosenmuller's fossa bilaterally appears to pose low risk to the adjacent hypoglossal nerves and parapharyngeal ICAs. Given consistently small intervals between lateral margins of the IUBF and exocranial hypoglossal foramen, intra-operative neuronavigation may be useful to minimize morbidity to the hypoglossal nerve. As a small subset of the population will exhibit marked medial ectasia of the parapharyngeal ICAs, CT angiography is recommended prior to surgery. With retraction of the soft palate and IUBF inferiorly, as described herein, the C1-2 joints could be accessed in the majority of specimens dissected with exposure of approximately 8 mm of the medial O-C1 and C1-2 joints.

EXAMPLES

Example 1

Cadaveric dissections were performed in 10 fresh frozen cadaveric heads. A rigid Storz (El Segundo, CA) zero-degree endoscope (4 mm diameter, 18 cm length) was utilized for endonasal visualization during the dissection. The nasopharynx was approached using a binostril approach with lateralization of the bilateral medial and inferior turbinates followed by resection of 2 cm of the posterior septum. In both specimens, a wide sphenoidotomy was performed following the limited posterior septectomy to facilitate the appropriate trajectory for cannulation described by Mendes et al. A 4 mm diamond Medtronic drill (Medtronic, Dublin, Ireland) was then used to remove the inferior portion of the posterior bony nasal septum flush with the floor of the nasal cavity. The bone of the posterior hard palate was thinned, and a silk tie or red rubber catheter was used to retract the soft palate to facilitate additional visualization of the posterior nasopharynx inferiorly.

Figure 7A:
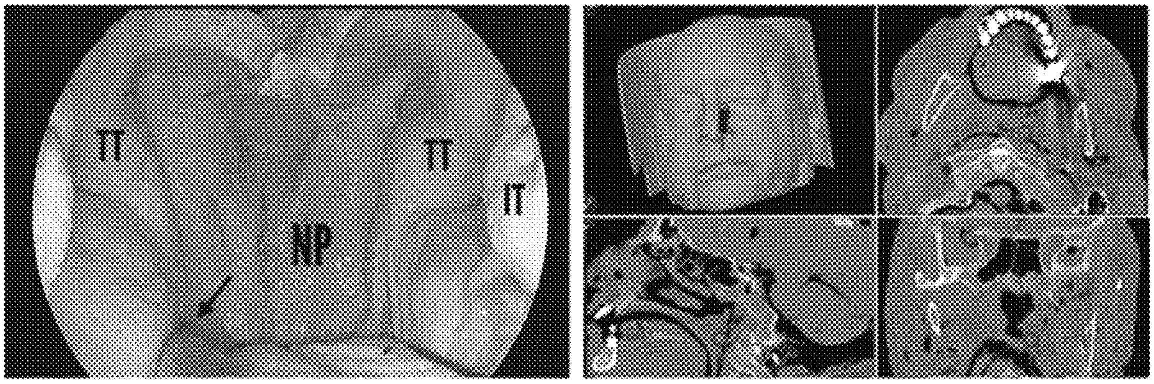
FIG. 7A is a series of images showing endonasal photographs in an embalmed cadaveric specimen summarizing regional landmarks used to guide the individual limbs of the IUBF and corresponding images from neuronavigation.
Figure 7B:
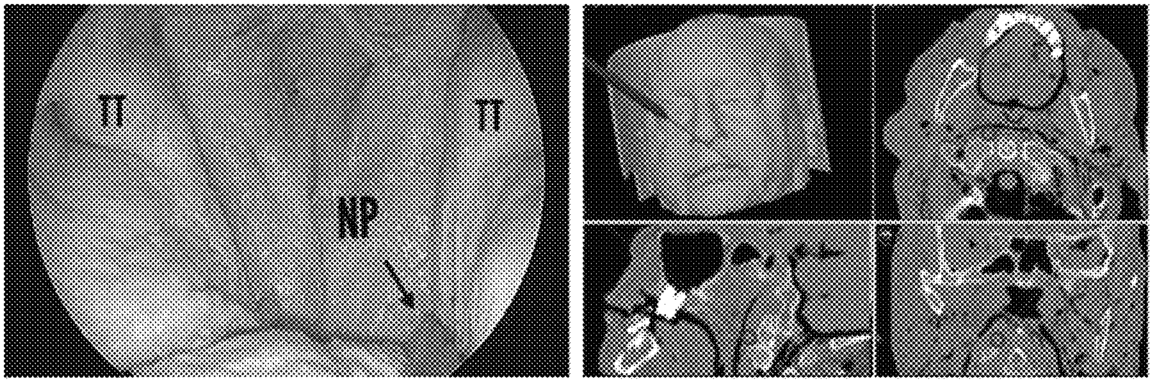
FIG. 7B is a series of images showing endonasal photographs in an embalmed cadaveric specimen summarizing regional landmarks used to guide the individual limbs of the IUBF and corresponding images from neuronavigation.
Figure 7C:
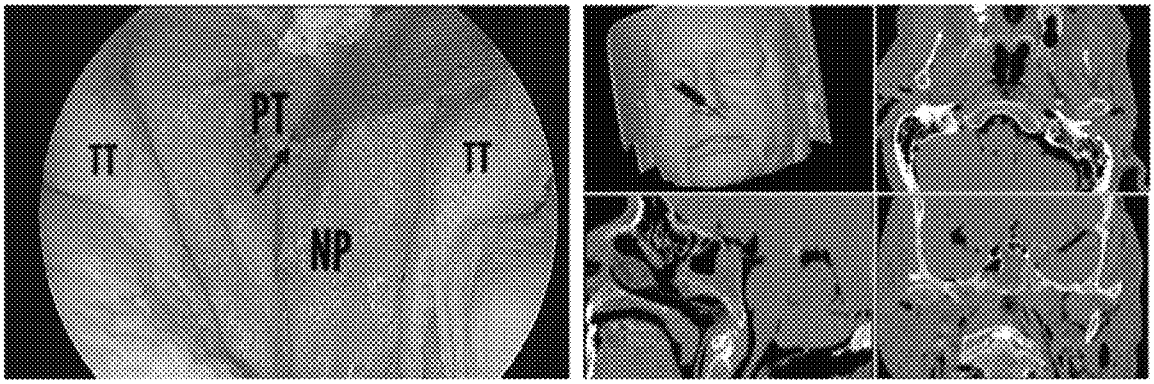
FIG. 7C is a series of images showing endonasal photographs in an embalmed cadaveric specimen summarizing regional landmarks used to guide the individual limbs of the IUBF and corresponding images from neuronavigation.

At this stage, regional anatomic landmarks were used to guide the individual limbs of the IUBF—as depicted in FIGS. 7A-7C. The lateral cuts were made in the Rosenmuller fossae bilaterally and extended as far inferiorly as visualization afforded by the hard and soft palate would allow. A superior incision was then used to connect the two lateral incisions at the level of the pharyngeal tubercle of the clivus using monopolar electrocautery. In the initial few specimens, we employed an approach which utilized two layers of dissection (layer 1: pharyngeal mucosa and constrictors, layer 2: longus capitus/colli), both retracted inferiorly, in attempts to minimize use of electrocautery near the hypoglossal foramen. With increased experience, it became clear that inferior reflection of an IUBF composed of a single layer was superior in terms of operative efficiency, gentler handling of tissue, and subsequent closure. Moreover, laboratory measurements indicated the exocranial hypoglossal foramina were consistently lateral to the IUBF.

Following the mucosal incisions discussed above, the IUBF could be elevated from underlying ligamentous structures using a straight curette. Dissection proceeded in the plane deep to both the pharyngeal constrictors and longus capitus muscle and the flap was retracted inferiorly using 4-0 prolene sutures delivered through the oral cavity. At this stage, the anterior atlanto-occipital membrane was immediately visible (FIG. 8B). Subperiosteal dissection of ligamentous structures with monopolar electrocautery permitted excellent visualization of the O-C1 joints (FIG. 8C). In the vast majority of specimens, retraction of the soft palate and IUBF into the oral cavity provided visualization of the C1-2 articulations. On occasion, upward mobilization of the C1 ring with a straight curette assisted with identification of the C1-2 articular surface. Visualization of articular surfaces could be expanded, as needed, by using additional soft tissue dissection laterally. Dissection at the level of the supracondylar groove then proceeded laterally in the plane deep to prevertebral musculature until it was possible to identify the exocranial presentation of the hypoglossal foramen. The anterior cortical wall of the hypoglossal canal was then drilled in the standard fashion to facilitate definitive verification of the position of the exocranial hypoglossal foramen.

At this stage, to facilitate precise caliper measurement of structures of the craniocervical junction, a LeFort 1 osteotomy was performed in the standard fashion. Briefly, a sublabial incision was made in the gingivobuccal mucosa to permit degloving of the upper lip and soft-tissues of the check. The mucoperichondria was elevated along the floor of the nasal cavity. Following subperichondrial dissection, a chisel was used to perform a LeFort 1 osteotomy without incorporation of a paramedian sagittal osteomy.

We then transitioned to an anterior sternocleidomastoideoproach to expose the proximal segment of the cervical ICA in the standard fashion. The cervical internal carotid arteries were meticulously dissected along their parapharyngeal course until their insertion at the skull base. The resultant wide operative exposure facilitated precise measurements of the parapharyngeal carotid arteries using caliper instrumentation. The following IUBF dimensions were assessed using caliper instrumentation: width of exposure at the top of the flap, width of exposure at the bottom of the flap, extent of O-C1 joint exposure, extent of C1-2 joint exposure (if visible). The distance between the hypoglossal canals was also recorded, as was the distance between the medial aspect of the carotid arteries at the levels of the pharyngeal tubercle and C1.

FIGS. 7A-7C show endonasal photographs in an embalmed cadaveric specimen summarizing regional landmarks used to guide the individual limbs of the IUBF and corresponding images from neuronavigation. FIG. 7A. (left) The arrow points to the tip of the neuronavigation probe, which identifies the inferior aspect of the right lateral incision of IUBF. (right) Corresponding neuronavigational images depicting location of tip of probe using axial, sagittal, and coronal non-contrast CT imaging. FIG. 7B. (left) The arrow points to the tip of the neuronavigation probe, which identifies the inferior aspect of the left lateral incision of IUBF. (right) Corresponding neuronavigational images depicting location of tip of probe using axial, sagittal, and coronal non-contrast CT imaging. FIG. 7C. (left) The arrow points to tip of the neuronavigation probe, which demonstrates the approximate location of the pharyngeal tubercle of the clivus (right) Corresponding neuronavigational images depicting location of tip of probe using axial, sagittal, and coronal non-contrast CT imaging. Of note, this embalmed specimen was used for illustrative purposes alone and not for attainment of data. Abbreviations: TT: torus tubarius, NP: nasopharynx, PT: pharyngeal tubercle, IT: inferior turbinate.

Figure 8A:
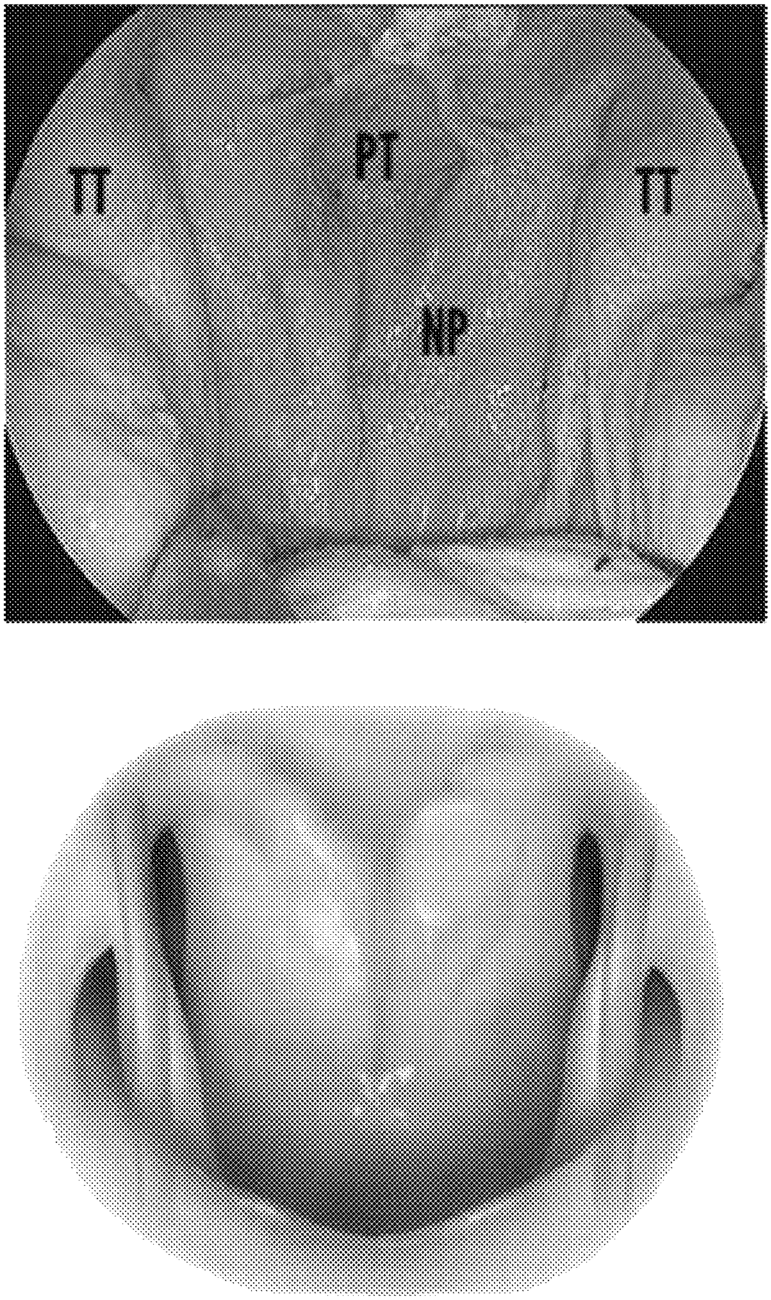
FIG. 8A is a pair of images showing endonasal cadaveric (top) and pictorial (bottom) images summarizing individual steps of the cadaveric dissection.
Figure 8B:
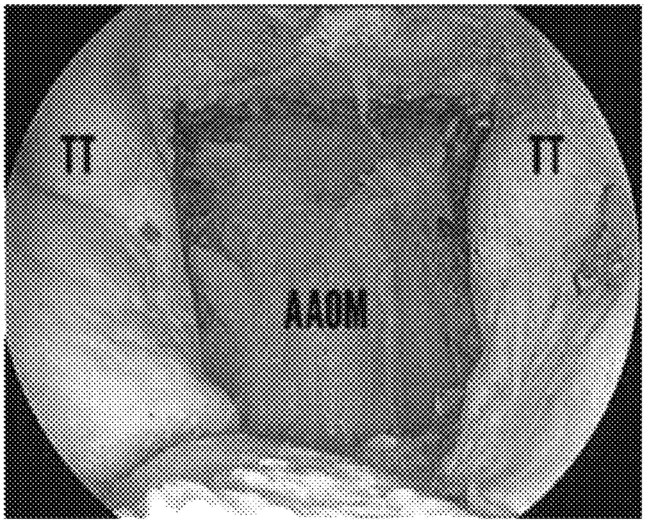
FIG. 8B is a pair of images showing endonasal cadaveric (top) and pictorial (bottom) images summarizing individual steps of the cadaveric dissection.
Figure 8B:
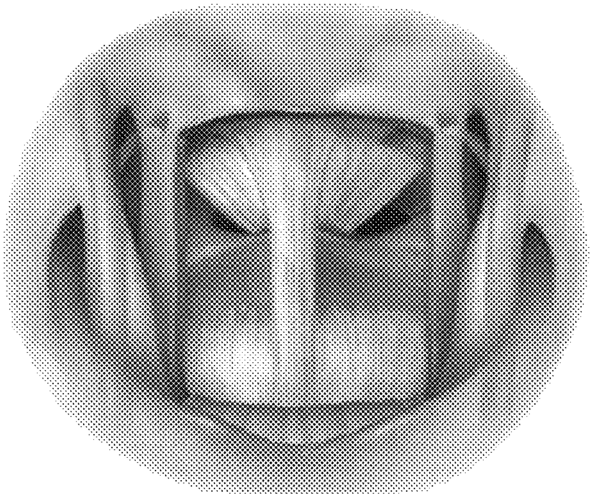
Figure 8C:
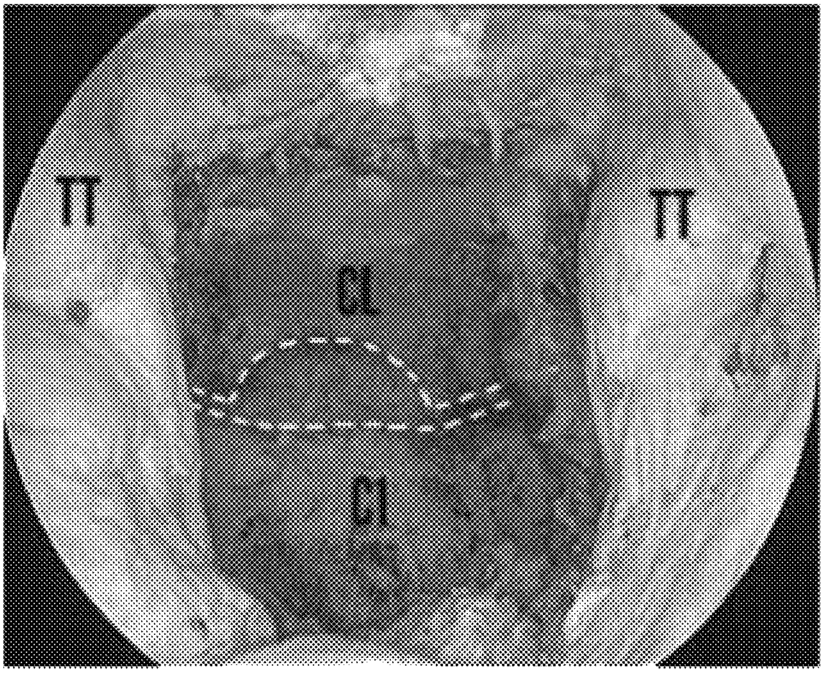
FIG. 8C is a pair of images showing endonasal cadaveric (top) and pictorial (bottom) images summarizing individual steps of the cadaveric dissection.
Figure 8C:
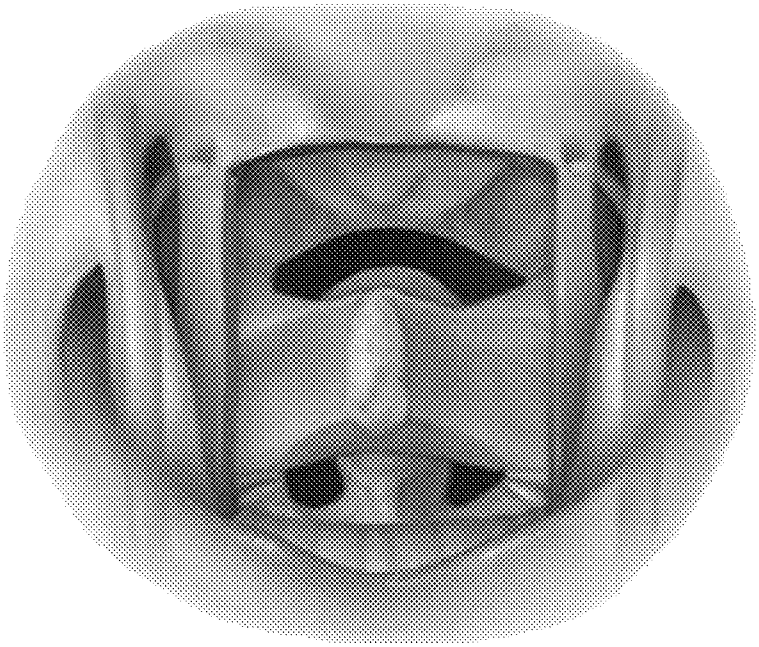

FIGS. 8A-8C show endonasal cadaveric (top) and pictorial (bottom) images summarizing individual steps of the cadaveric dissection. FIG. 8A: View of the posterior nasopharynx with a zero-degree endoscope following posterior septectomy and retraction of the soft palate. FIG. 8B: View of anterior atlanto-occipital membrane following retraction of soft palate and IUBF inferiorly. FIG. 8C: View after subperiosteal dissection and removal of associated ligamentous structures. Standard anatomical position of the hypoglossal foramina and nerves and parapharyngeal internal carotid arteries is depicted in the pictorial image (bottom). Abbreviations: TT: torus tubarius, PT: pharyngeal tubercle, NP: nasopharynx, AAOM: Anterior atlanto-occipital membrane, CL: Clivus, C1: C1 vertebra.

Results from Example 1 are summarized in Table 1. The following measurements were obtained: on average, the widths at the top and bottom of the flap were 26.0 mm and 29.1 mm respectively. In the ten cadaveric specimens, the IUBF facilitated exposure of approximately 8.5/8.6 mm of the medial surfaces of the respective right/left C1-2 joints and 8.2/8.3 mm of the medial surfaces of the respective right/left O-C1 joints. The mean distances between the carotid arteries at the supracondylar groove and C1 were 39.5 mm and 39.8 mm respectively. The mean distance between the hypoglossal canals was 33.7 mm. A composite illustration of the numerous anatomic relationships reported above can be found in FIG. 9.

Figure 9:
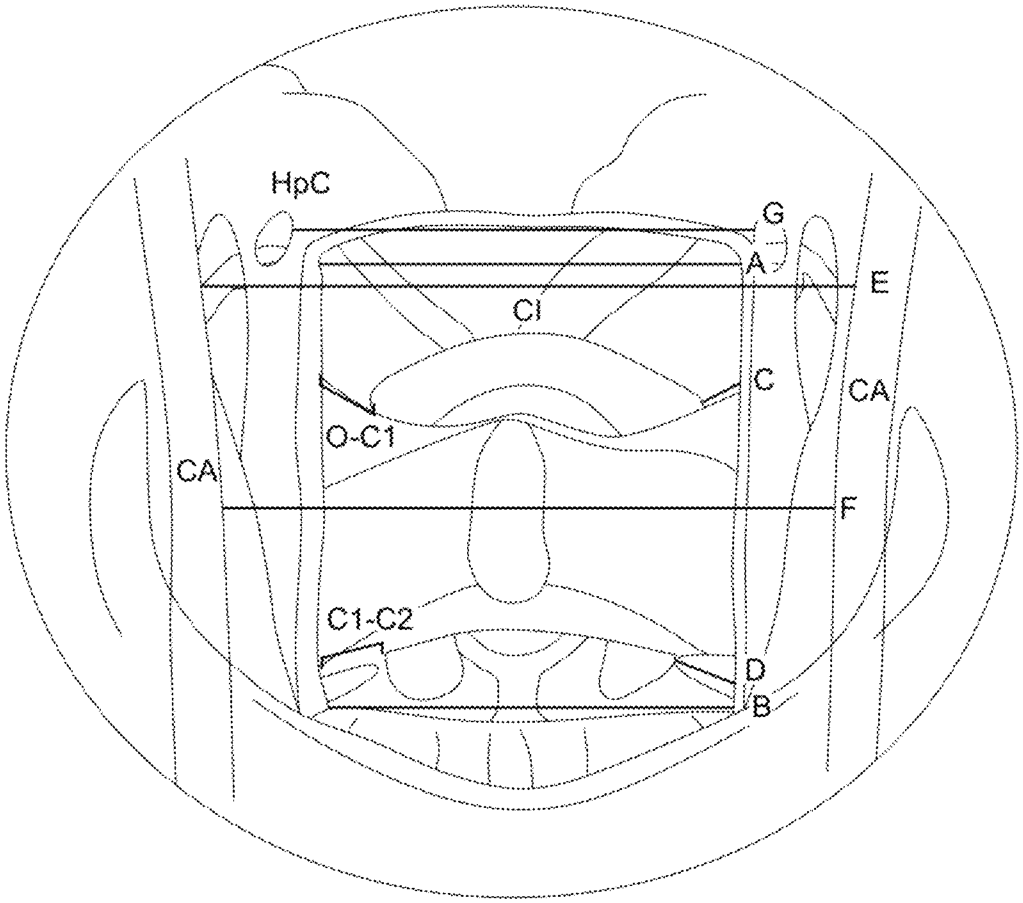
FIG. 9 is a schematic image summarizing all recorded measurements and anatomic relationships.

FIG. 9 shows a schematic image summarizing all recorded measurements and anatomic relationships. A: Width top of flap; B: Width bottom of flap; C: Extent O-C1 joint exposure; D: Extent C1-C2 joint exposure; E: Distance between carotids at SCG; F: Distance between carotids at C1; G: Distance between hypoglossal canal. CA: Carotid artery, CL: Clivus, HpC: hypoglossal canal, O-C1: atlanto-occipital joint, C1-C2: C1-C2 vertebral joint.

In all specimens evaluated, the lateral limbs of the flap did not intersect with the parapharyngeal carotid arteries; however, in 3 of the 10 specimens evaluated, the parapharyngeal carotid artery was noted to reside <5 mm lateral to the lateral limb of the incision (Table 2). In all specimens evaluated, the lateral limbs of the flap did not intersect with the extracranial hypoglossal foramina. However, in seven of ten cadaver heads, the lateral limb of the IUBF at the level of the supracondylar groove was noted to be <5 mm medial to the HC. In all specimens, the entry point of the transarticular screw reported by Mendes et al. (reported as 6.0+/−1.0 mm lateral to the medial border of the C-1 lateral mass and 9.0+/−1.9 mm superior to the C1-2 joint,) was accessible following IUBF exposure.

TABLE 1

| Spec. | WTF (mm) | WBF (mm) | O-C1 JE (R/L) | C1-2 JE (R/L) | DBC (SCG) | DBC (C1) | DBHC |
|---|---|---|---|---|---|---|---|
| 1 | 25 mm | 29 mm | 8/8 mm | 9/9 mm | 36 mm | 38 mm | 32 mm |
| 2 | 23 mm | 28 mm | 7/7 mm | 10/10 mm | 41 mm | 41 mm | 34 mm |
| 3 | 27 mm | 32 mm | 10/10 mm | 10/10 mm | 35 mm | 36 mm | 35 mm |
| 4 | 29 mm | 31 mm | 9/10 mm | 8/9 mm | 39 mm | 42 mm | 32 mm |
| 5 | 24 mm | 27 mm | 7/7 mm | NV | 39 mm | 38 mm | 30 mm |
| 6 | 26 mm | 28 mm | 8/8 mm | 7/8 mm | 42 mm | 38 mm | 35 mm |
| 7 | 25 mm | 28 mm | 8/7 mm | 9/9 mm | 39 mm | 41 mm | 35 mm |
| 8 | 26 mm | 30 mm | 8/9 mm | 7/7 mm | 40 mm | 39 mm | 36 mm |
| 9 | 27 mm | 29 mm | 9/9 mm | NV | 42 mm | 42 mm | 35 mm |
| 10 | 28 mm | 29 mm | 8/8 mm | 8/7 mm | 42 mm | 43 mm | 33 mm |
| Avg. | 26.0 mm | 29.1 mm | 8.2/8.3 mm | 8.5/8.6 mm | 39.5 mm | 39.8 mm | 33.7 mm |

Table 1: Cadaveric measurements of IUBF and related anatomic landmarks. WTF: width of top of flap, WBF: width of bottom of flap, O-C1 JE: width of O-C1 joint exposure, C1-C2 JE: width of C1-2 joint exposure, DBC (SHG): distance between carotids at supracondylar groove, DBC: distance between carotids at C1, DBHC: distance between hypoglossal canals. NV: not visible.

TABLE 2

| Specimen | LM of IUBF < 5 mm to CA? | LM of IUBF < 5 mm to HC? | Able to perform trans-articular C1-2 screw? |
|---|---|---|---|
| 1 | Yes | Yes | Yes |
| 2 | No | No | Yes |
| 3 | Yes | Yes | Yes |
| 4 | No | Yes | Yes |
| 5 | No | Yes | Yes |
| 6 | No | Yes | Yes |
| 7 | No | No | Yes |
| 8 | Yes | No | Yes |
| 9 | No | Yes | Yes |
| 10 | No | Yes | Yes |

Table 2: Table categorizing IUBF incisions in reference to (1) close proximity to carotid artery (CA). (2) close proximity to hypoglossal canal (HC), and (3) ability to perform transarticular screw. LM: lateral margin. IUBF: inverted u-shaped buccopharyngeal flap (IUBF), CA: carotid artery. HC: hypoglossal canal.

Example 2: Illustrative Endonasal Odontoidectomy Case

Figure 12A:
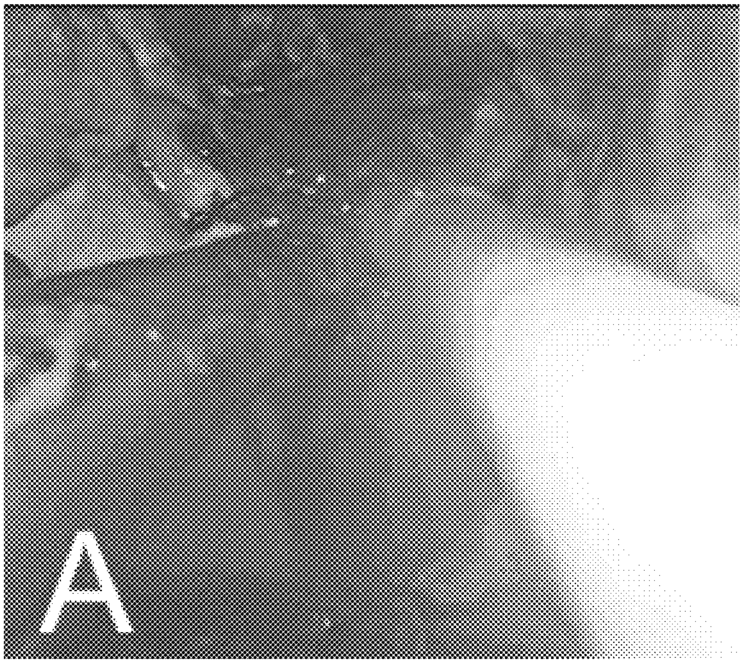
FIG. 12A is an image showing an endonasal view of posterior nasopharynx in a patient previously treated with a posterior decompression and instrumented craniocervical fusion.
Figure 12B:
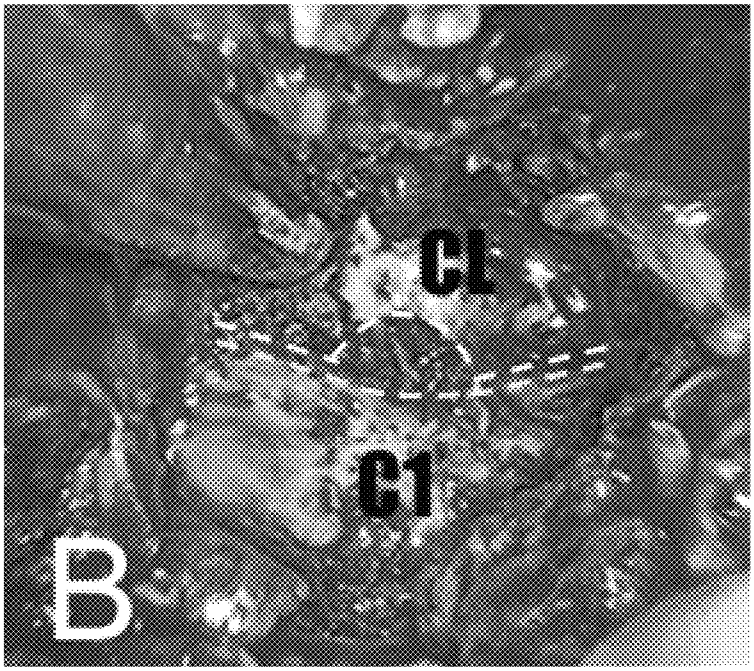
FIG. 12B is an image after the IUNF has been elevated and retracted downward, ligamentous structures of the CCJ are removed-exposing the clivus (CL), medial O-C1 joints, and C1.
Figure 12C:
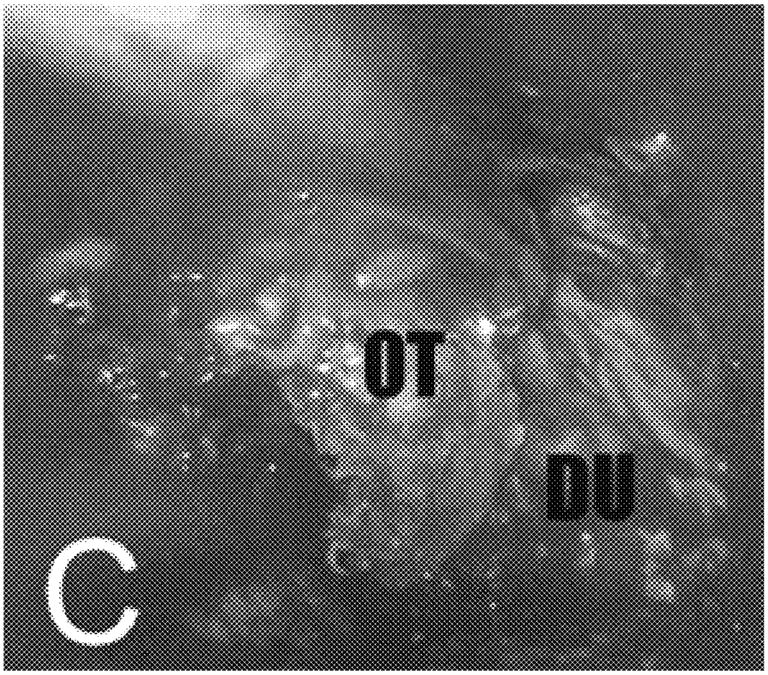
FIG. 12C is an image showing that wide visualization facilitates removal of the odontoid tip (OT) with the underlying dura (DU) visible.
Figure 12D:
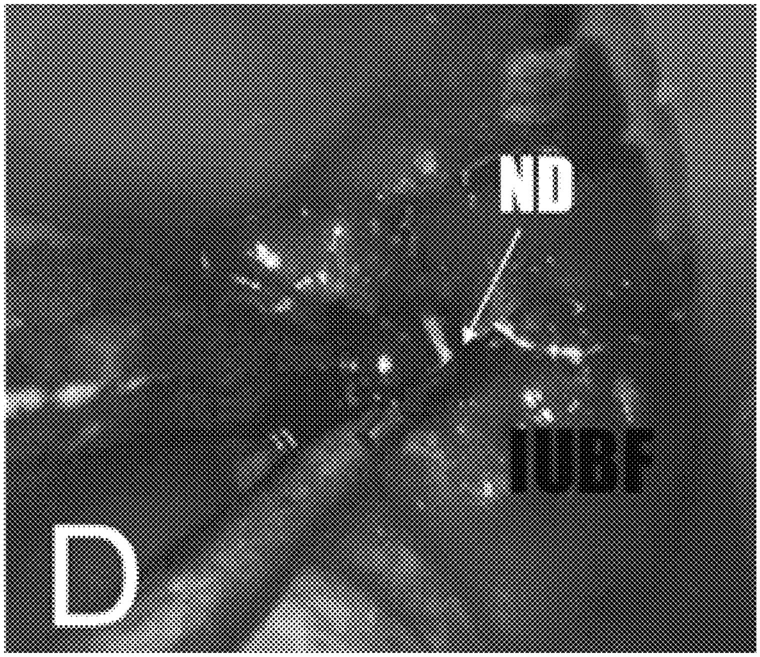
FIG. 12D is an image showing that the IUNF is resuspended using barbed suture with tabs and endonasal needle driver (ND).
Figure 12E:
FIG. 12E is an image showing pre-operative sagittal non-contrast CT imaging.
Figure 12F:
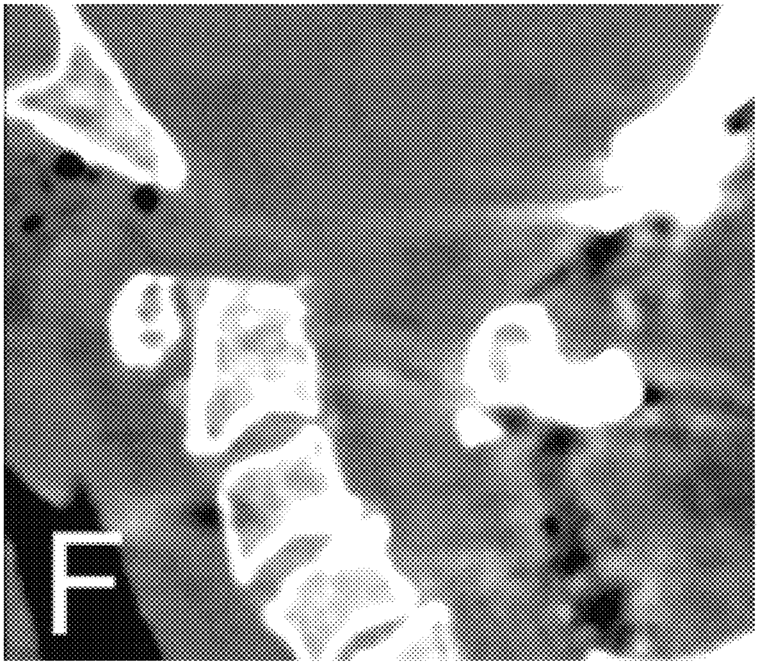
FIG. 12F is an image showing post-operative sagittal non-contrast CT imaging.

A 67 year-old female with a history of rheumatoid arthritis, atrial fibrillation, acquired basilar invagination, and a remote history of posterior decompression (suboccipital craniectomy and C1 laminectomy) and occipital to C3 fusion in 2019 presented with progression in neck pain and persistent difficulty with swallowing, upper extremity numbness, and gait imbalance. On examination, bilateral weakness in hand intrinsics (4+/5) and ataxic gait was noted. Imaging demonstrated basilar invagination with pB-C2 line of 12 mm (FIG. 12E) and pseudarthrosis with screw haloing at C2-3. Prior to surgery, a CT angiogram was obtained for neuronavigation. The patient was taken to the OR for stage 1 revision of fusion construct with extension from occiput to C5 with stage 2 endonasal odontoidectomy. During stage 2, an IUNF was turned (FIG. 12A) using anatomic landmarks previously described and reflected inferiorly. The clivus, C1 ring, and medial occiptocervical articulations were visible-facilitating ventral decortication in setting of pseudarthrosis (FIG. 12B). The rostral portion of C1 ring and odontoid were resected in the standard fashion without complication (FIG. 12C). Following odontoidectomy, the IUNF was resuspended using two barbed, tabbed 3-0 PDS sutures (Ethicon; Blue Ash, OH) delivered via endonasally-compatible needle driver (FIG. 12D). Patient was extubated following surgery and resumed a normal diet on POD1. She was discharged from the hospital on post-operative day 5. Post-operative CT demonstrated appropriate ventral decompression (FIG. 12F). Six months following surgery, she reported improvement in her pre-operative neck pain as well as subjective improvement in swallowing function and balance.

FIG. 12: A. Endonasal view of posterior nasopharynx in patient previously treated with a posterior decompression and instrumented craniocervical fusion; bovie electrocautery used to make superior incision in IUNF. B. After the IUNF has been elevated and retracted downward, ligamentous structures of the CCJ are removed-exposing the clivus (CL), medial O-C1 joints, and C1. C. Wide visualization facilitates removal of the odontoid tip (OT); underlying dura (DU) visible. D. Following decompression, the IUNF is resuspended using barbed suture with tabs and endonasal needle driver (ND). E. Pre- and F. post-operative sagittal non-contrast CT imaging.

Having shown and described various embodiments of the present invention, further adaptations of the methods and systems described herein may be accomplished by appropriate modifications by one of ordinary skill in the art without departing from the scope of the present invention. For instance, the examples, embodiments, geometrics, materials, dimensions, and the like discussed above are illustrative and are not required. Accordingly, the scope of the present invention should be considered in terms of the following claims and is understood not to be limited to the details of structure and operation shown and described in the specification and drawings.

What is claimed is:

1. An atlanto-occipital fusion method for fixating a 0-C1 joint, comprising:

a. preparing an endonasal surgical path using a binostril approach comprising:
   i. removing the inferior portion of the posterior septum,
   ii. performing a myomucosal flap incision to create a flap,
   iii. retracting the flap to expose the O-C1 joint,
b. bilaterally decorticating the O-C1 joint, and
c. inserting an implant into each side of the decorticated 0-C1 joint;

wherein the implant comprises an implant system; the implant system comprising:

x. a plate comprising a horizontal panel, a right vertical panel and a left vertical panel;
   i. the horizontal panel defining at least a first opening and a second opening;
   ii. the right vertical panel defining at least a first right vertical panel opening and a second right vertical panel opening;
   iii. the left vertical panel defining at least a first left vertical panel opening and a second left vertical panel opening; and
y. at least four bone fixation fasteners;
   iv. a first fastener disposed with both the first opening and the first right vertical panel opening;
   v. a second fastener disposed with both the second opening and the first left vertical panel opening;
   vi. a third fastener disposed with the second right vertical panel opening;
   vii. a fourth fastener disposed with the second left vertical panel opening; wherein the first fastener is engageable with the plate and capable of fixing with the C1 lateral mass, the second fastener is engageable with the plate and capable of fixing with the C1 lateral mass, the third fastener is engageable with the plate and capable of fixing with the occipital condyle, and the fourth fastener is engageable with the plate and capable of fixing with the occipital condyle.

2. The method of claim 1 wherein the plate of the implant system comprises a material selected from the group consisting of carbon fiber, polylactic acid, stainless steel alloys, commercially pure titanium, titanium alloys, ceramics, thermoplastics, polyethylene terephthalate (PET), fabric, silicone, polyurethane, silicone-polyurethane copolymers, polymeric rubbers, polyolefin rubbers, hydrogels, semi-rigid and rigid materials.

3. The method of claim 1 wherein the plate of the implant system comprises carbon fiber.

4. The method of claim 1 wherein the bone fixation fasteners of the implant system are selected from the group consisting of bone screws, helical nails, distally expanding nails, and distally expanding screws.

* * * * *